(12) United States Patent
Bierman et al.

(10) Patent No.: US 8,277,420 B2
(45) Date of Patent: Oct. 2, 2012

(54) SECUREMENT DEVICE WITH TOGGLE CLAMP MECHANISM

(75) Inventors: Steven F. Bierman, Del Mar, CA (US); Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

(21) Appl. No.: 12/480,557

(22) Filed: Jun. 8, 2009

(65) Prior Publication Data
US 2009/0306603 A1    Dec. 10, 2009

Related U.S. Application Data

(60) Provisional application No. 61/060,073, filed on Jun. 9, 2008.

(51) Int. Cl.
*A61M 5/32* (2006.01)

(52) U.S. Cl. ........................................ 604/178; 604/174

(58) Field of Classification Search ........... 604/178–180
See application file for complete search history.

(56) References Cited

U.S. PATENT DOCUMENTS

| | | |
|---|---|---|
| 2,525,398 A | 10/1950 | Collins |
| 2,533,961 A | 12/1950 | Rousseau et al. |
| 2,707,953 A | 5/1955 | Ryan |
| 3,059,645 A | 10/1962 | Hasbrouck et al. |
| 3,064,648 A | 11/1962 | Bujan |
| 3,482,569 A | 12/1969 | Raffaelli |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |
| 3,766,915 A | 10/1973 | Rychlik |
| 3,834,380 A | 9/1974 | Boyd |
| 3,856,020 A | 12/1974 | Kovac |
| 3,863,527 A | 2/1975 | Berning |
| 3,906,946 A | 9/1975 | Nordström |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,129,128 A | 12/1978 | McFarlane |
| 4,142,527 A | 3/1979 | Garcia |
| 4,161,177 A | 7/1979 | Fuchs |

(Continued)

FOREIGN PATENT DOCUMENTS

EP         0064284 A2    11/1982

(Continued)

*Primary Examiner* — Kevin C Sirmons
*Assistant Examiner* — Brandy C Scott
(74) *Attorney, Agent, or Firm* — Knobbe Martens Olson & Bear, LLP

(57) ABSTRACT

A securement device for securing a medical article includes two supports extending from a base. Lever arms extend from each of the supports. One or both of the lever arms include a channel portion. The lever arms are pivotable about the ends of the supports to define an open position and a closed position. In the open position, the lever arms extend generally upwardly from the supports. In the closed position, the lever arms extend generally downwardly from the supports, and the channel portion or portions at least partially surround the medical article. As the lever arms move from the open position to the closed position, they exert an outward force on the ends of the supports.

43 Claims, 14 Drawing Sheets

U.S. PATENT DOCUMENTS

| | | | |
|---|---|---|---|
| 4,165,748 A | 8/1979 | Johnson |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,275,721 A | 6/1981 | Olson |
| 4,284,076 A | 8/1981 | Hall |
| 4,316,461 A | 2/1982 | Marais et al. |
| 4,326,519 A | 4/1982 | D'Alo et al. |
| 4,333,468 A | 6/1982 | Geist |
| 4,362,156 A | 12/1982 | Feller et al. |
| 4,392,853 A | 7/1983 | Muto |
| 4,397,647 A | 8/1983 | Gordon |
| 4,405,312 A | 9/1983 | Gross et al. |
| 4,449,975 A | 5/1984 | Perry |
| 4,453,933 A | 6/1984 | Speaker |
| 4,480,639 A | 11/1984 | Peterson et al. |
| 4,627,842 A | 12/1986 | Katz |
| 4,683,882 A | 8/1987 | Laird |
| 4,711,636 A | 12/1987 | Bierman |
| 4,737,143 A | 4/1988 | Russell |
| 4,742,824 A | 5/1988 | Payton et al. |
| 4,792,163 A | 12/1988 | Kulle |
| 4,808,162 A | 2/1989 | Oliver |
| 4,822,342 A | 4/1989 | Brawner |
| 4,832,019 A | 5/1989 | Weinstein et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,700 A | 12/1990 | Tollini |
| 4,986,815 A | 1/1991 | Schneider |
| 5,037,397 A | 8/1991 | Kalt et al. |
| 5,069,206 A | 12/1991 | Crosbie |
| 5,073,170 A | 12/1991 | Schneider |
| 5,084,026 A * | 1/1992 | Shapiro ........................ 604/179 |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,236,421 A | 8/1993 | Becher |
| 5,266,401 A | 11/1993 | Tollini |
| 5,267,967 A | 12/1993 | Schneider |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman et al. |
| 5,322,097 A | 6/1994 | Wright |
| 5,338,308 A | 8/1994 | Wilk |
| 5,342,317 A | 8/1994 | Claywell |
| 5,344,406 A | 9/1994 | Spooner |
| 5,352,211 A | 10/1994 | Merskelly |
| 5,354,282 A | 10/1994 | Bierman |
| 5,372,589 A | 12/1994 | Davis |
| 5,380,293 A | 1/1995 | Grant |
| 5,380,395 A | 1/1995 | Uchida |
| 5,382,239 A | 1/1995 | Orr et al. |
| 5,402,776 A | 4/1995 | Islava |
| 5,403,285 A | 4/1995 | Roberts |
| 5,413,562 A | 5/1995 | Swauger |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,578,013 A | 11/1996 | Bierman |
| 5,593,395 A | 1/1997 | Martz |
| 5,637,098 A | 6/1997 | Bierman |
| 5,685,859 A | 11/1997 | Kornerup |
| 5,693,032 A | 12/1997 | Bierman |
| 5,722,959 A | 3/1998 | Bierman |
| 5,755,225 A * | 5/1998 | Hutson ................... 128/207.18 |
| 5,810,781 A | 9/1998 | Bierman |
| 5,833,666 A | 11/1998 | Davis et al. |
| 5,911,707 A | 6/1999 | Wolvek et al. |
| 6,067,985 A | 5/2000 | Islava |
| 6,132,399 A | 10/2000 | Shultz |
| 6,213,979 B1 | 4/2001 | Bierman |
| 6,228,064 B1 | 5/2001 | Abita et al. |
| 6,231,547 B1 | 5/2001 | O'Hara |
| 6,283,945 B1 | 9/2001 | Bierman |
| 6,287,281 B1 | 9/2001 | Nishtala et al. |
| 6,428,515 B1 | 8/2002 | Bierman et al. |
| 6,488,664 B1 | 12/2002 | Solomon et al. |
| 6,491,664 B2 | 12/2002 | Bierman |
| 6,582,403 B1 | 6/2003 | Bierman et al. |
| 7,413,561 B2 | 8/2008 | Raulerson et al. |
| 2001/0011164 A1 | 8/2001 | Bierman |
| 2002/0165493 A1 | 11/2002 | Bierman |
| 2003/0229313 A1 | 12/2003 | Bierman |
| 2007/0173766 A1 | 7/2007 | Bierman |
| 2009/0254040 A1 | 10/2009 | Bierman et al. |
| 2009/0299294 A1 * | 12/2009 | Pinkus ......................... 604/177 |

FOREIGN PATENT DOCUMENTS

| | | |
|---|---|---|
| EP | 356683 A1 | 3/1990 |
| FR | 2381529 | 2/1978 |
| GB | 2086466 | 5/1982 |
| GB | 2211417 | 7/1989 |
| WO | WO 80/01458 | 7/1980 |
| WO | WO 92/19309 | 11/1992 |
| WO | WO 94/12231 | 6/1994 |
| WO | WO 97/15342 | 5/1997 |
| WO | WO 2008/151047 A1 | 12/2008 |

* cited by examiner

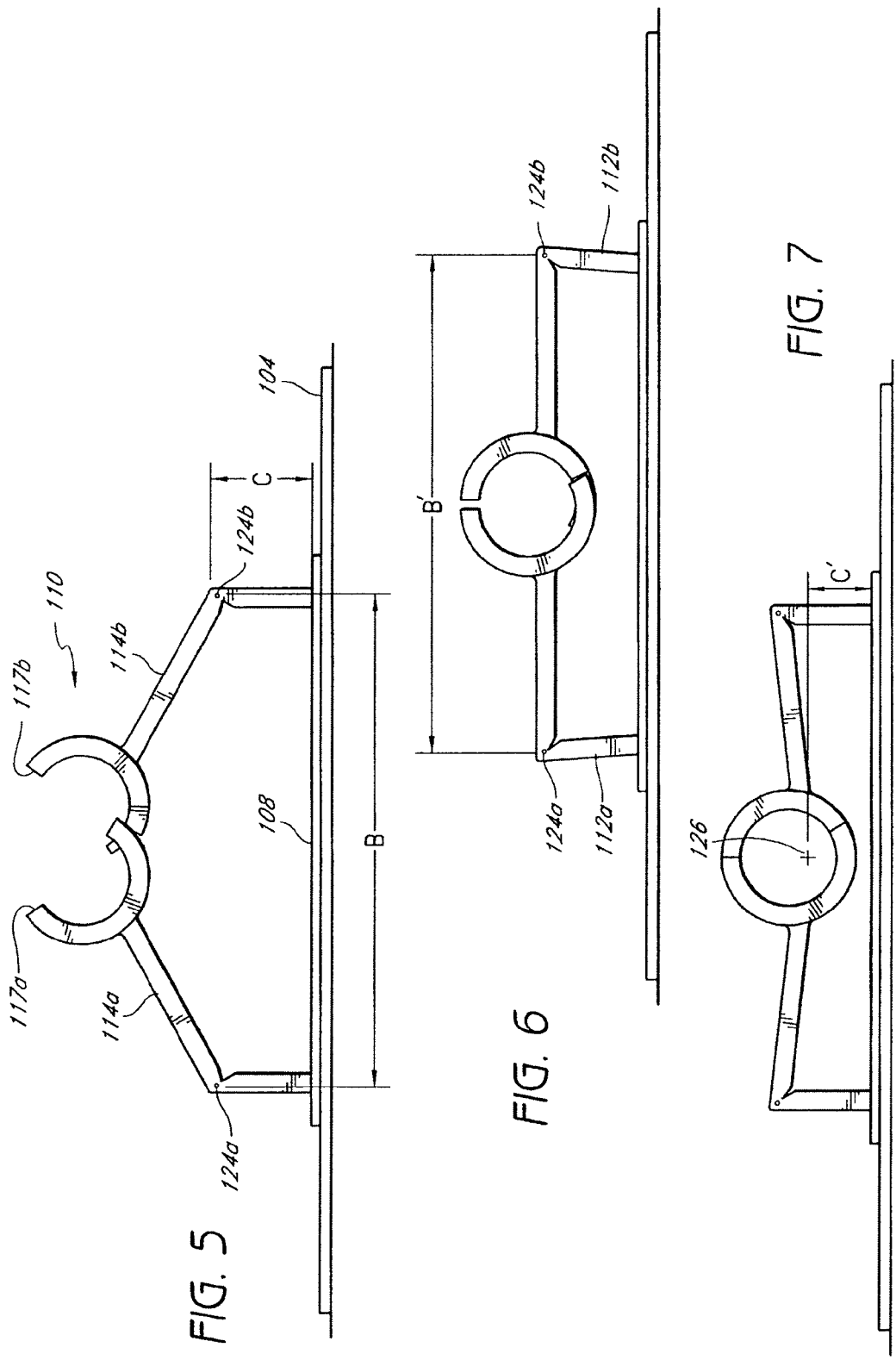

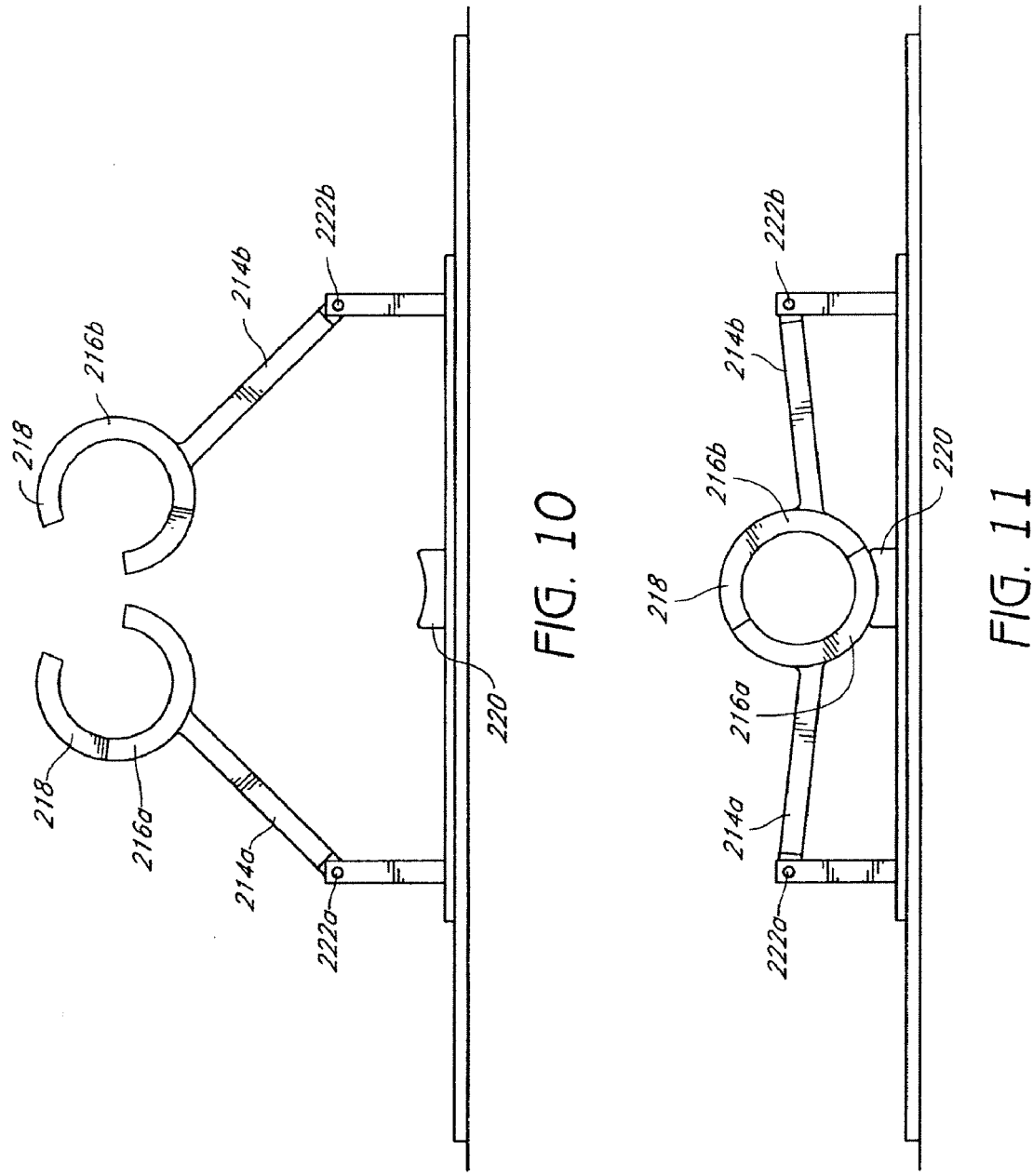

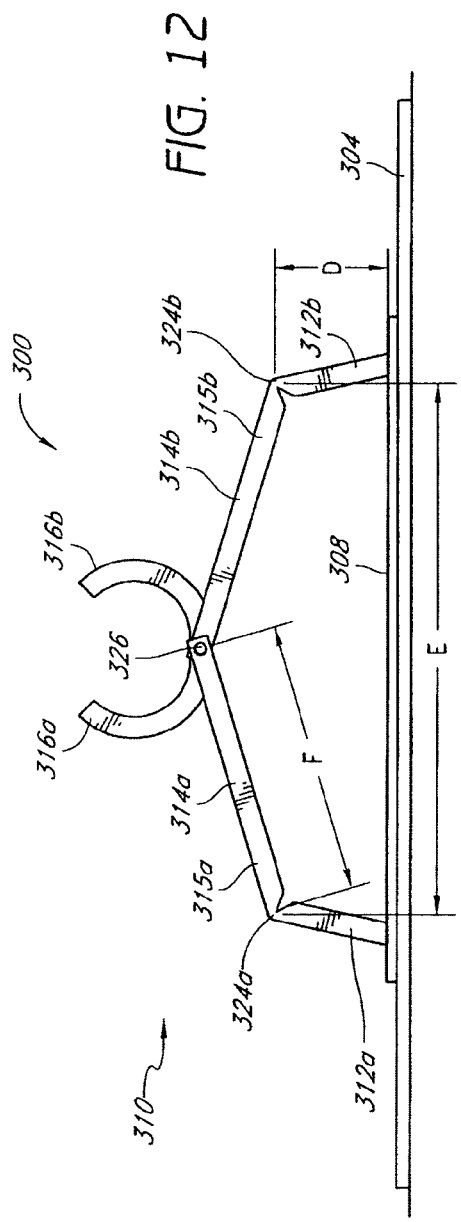
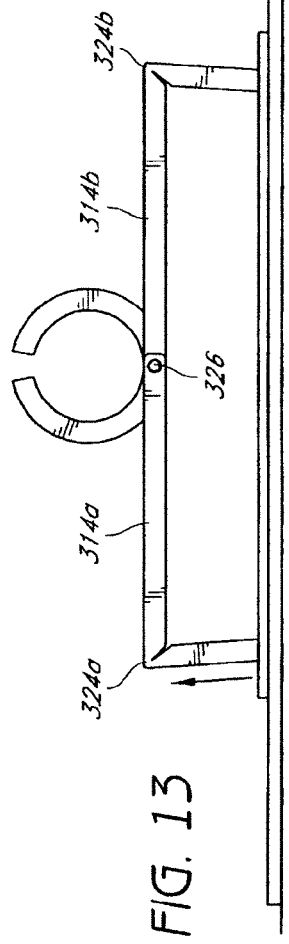
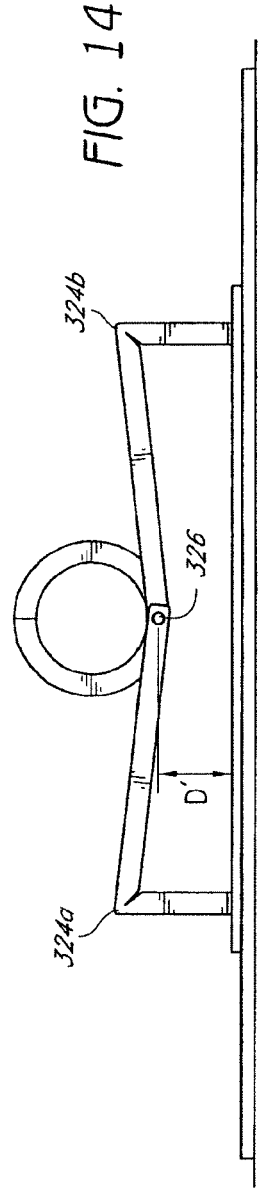

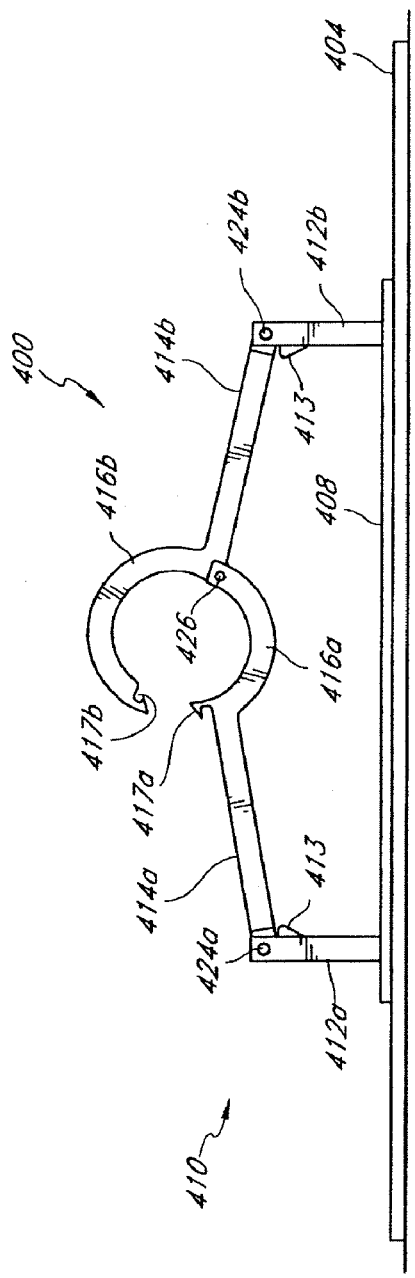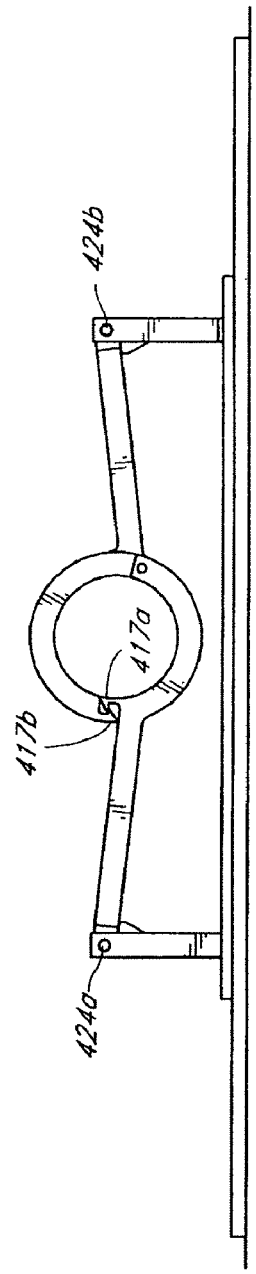

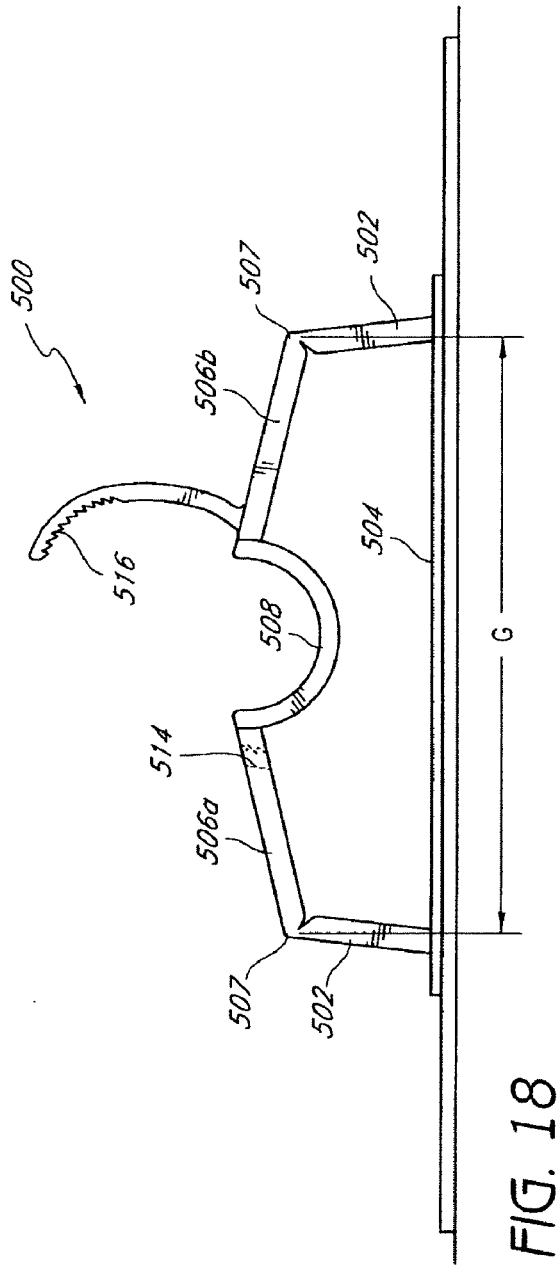
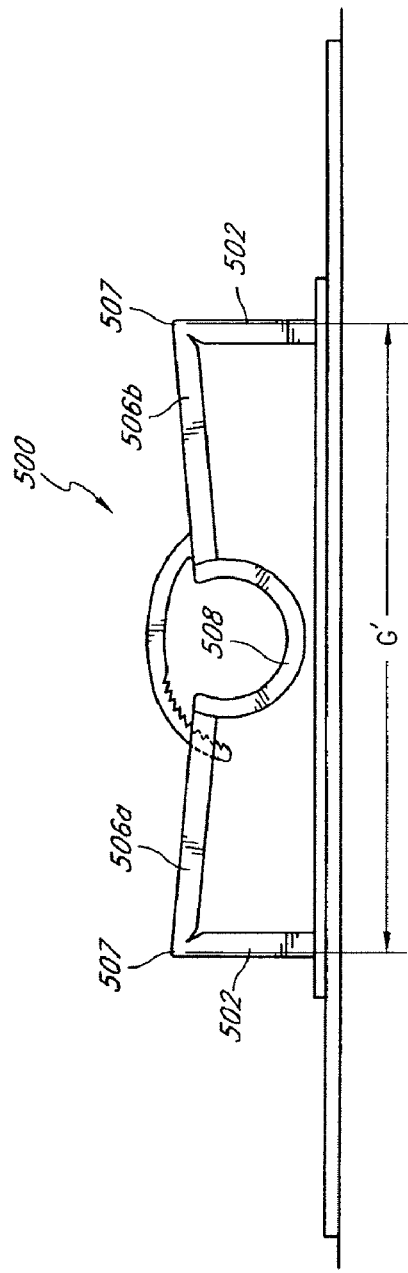

SECUREMENT DEVICE WITH TOGGLE CLAMP MECHANISM

CROSS-REFERENCE TO RELATED APPLICATIONS

This application claims the benefit under 35 U.S.C. §119(e) of U.S. Provisional Application No. 61/060,073, filed Jun. 9, 2008, which is hereby expressly incorporated by reference in its entirety.

BACKGROUND OF THE INVENTION

1. Field

This application relates to a securement device for securing a medical article to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical article properly positioned for the duration of treatment, the catheter or medical article can be secured to the patient in a variety of ways. Most commonly, this involves taping or suturing the catheter or medical article to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin. Such repeated applications of tape over the catheter or medical article can additionally lead to the build up of adhesive residue on the outer surface of the catheter or medical article. This residue can result in contaminants adhering to the medical article itself, increasing the likelihood of infection of the insertion site. This residue can also make the catheter or medical article stickier and more difficult to handle for healthcare providers.

Suturing also carries risk, both to healthcare workers and patients. Healthcare workers can suffer accidental needlestick injury, which may expose them to hepatitis, HIV, and other pathogens. Patients can suffer local or even systemic infection from suture, as well as scarring and pain.

Therefore, an improved system that obviates tape and suture is desired for securement of catheters and other medical articles.

SUMMARY

The systems and methods disclosed herein have several features, no single one of which is solely responsible for its desirable attributes. Without limiting the scope as expressed by the claims that follow, its more prominent features will now be discussed briefly.

In one aspect, a securement device for securing a medical article is provided. The device comprises a base, and first and second supports extending away from the base, each of the first and second supports having a distal end which is spaced apart from the base. The device also comprises a first lever arm pivotable about the distal end of the first support, the first lever arm comprising a first channel portion, and a second lever arm pivotable about the distal end of the second support, the second lever arm comprising a second channel portion. The first and second lever arms are movable between an open position, in which the first and second lever arms extend above a line defined by the distal ends of the supports, and a closed position, in which the first and second lever arms extend below the line. The first and second channel portions cooperate to define a receiving area for the medical article when in the open position and cooperate to at least partially surround the medical article when in the closed position.

In another aspect, retainer for securing a medical article is provided. The retainer comprises a base, a first support extending from the base, a second support extending from the base, a first lever arm coupled to the first support at a first point, a second lever arm coupled to the second support at a second point, and at least one channel portion coupled to at least one of the first and second lever arms. At least a portion of the retainer is movable between a first position, in which the first and second lever arms extend generally upward of the first and second points, and a second position, in which the first and second lever arms extend generally downward of the first and second points. The at least one channel portion is configured to at least partially surround the medical article when the retainer is in the second position.

In yet another aspect, a securement device for securing a medical article is provided. The device comprises a retainer having a first portion and a second portion disposed above a base. The first and second portions are movable in at least a transverse direction with respect to first and second points to define an open position and a closed position. The first and second points are spaced apart from the base. The first and second portions extend generally away from the first and second points when in the open position. The first and second portions extend generally downwardly from the first and second points when in the closed position. The first and second portions cause the first and second points to move laterally outward as the first and second portions move from the open position to the closed position. The first and second portions define a channel in the closed position, the channel being configured to at least partially surround the medical article in the closed position.

In still another aspect, a method of securing a medical article to a patient is provided. The method comprises providing a retainer comprising a base, first and second supports extending upwardly from the base, a first lever arm pivotable about a distal region of the first support, a second lever arm pivotable about a distal region of the second support, a first channel portion movable with the first lever arm, a second channel portion movable with the second lever arm, the first and second lever arms being movable between an open position, in which the first and second lever arms extend above a line defined by the distal ends of the supports, and a closed position, in which the first and second lever arms extend below the line, the first and second channel portions configured to allow placement of the medical article therebetween in the open position, the first and second channel portions cooperating to at least partially surround the medical article in the closed position. The method also comprises placing the medical article between at least portions of the first and second channel portions when in an open position, and applying downward force on at least one of the medical article and the retainer so as to move the lever arms past an intermediate position in which the lever arms are horizontally aligned and into the closed position.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

The above-mentioned and other features of the invention will now be described with reference to the drawings of various embodiments which are intended to illustrate but not to limit the invention. The drawings contain the following figures:

FIG. 5 is a front view of the securement device of FIG. 1 in an open position.

FIG. 6 is a front view of the securement device of FIG. 1 shown in an intermediate (center) position, with the lever arms extending horizontally in line with one another.

FIG. 7 is a front view of the securement device of FIG. 1 shown in a clamped (over-center) position.

FIG. 10 is a front view of the securement device of FIG. 9 in an open position.

FIG. 11 is a front view of the securement device of FIG. 9 shown in a locked or clamped position.

FIG. 12 is a front view of a securement device configured in accordance with another preferred embodiment of the present invention, shown in an open position.

FIG. 13 is a front view of the securement device of FIG. 12 shown in an intermediate (horizontal) position.

FIG. 14 is a front view of the securement device of FIG. 12 shown in a locked or clamped position.

FIG. 15 is a front view of a securement device configured in accordance with another preferred embodiment of the present invention, shown in an open position.

FIG. 16 is a front view of the securement device of FIG. 15 shown in a locked or clamped position.

FIG. 18 is a front view of the device of FIG. 17 shown in an open position.

FIG. 19 is a front view of the device of FIG. 17 shown in a locked or clamped position.

DETAILED DESCRIPTION OF THE PREFERRED EMBODIMENTS

The following description and the accompanying figures, which describe and show the preferred embodiments, are made to demonstrate several possible configurations that a securement device can take to include various aspects and features of the invention. The illustrated embodiments are shown in use with illustrative examples of a medical line. The illustration of securement devices in this context is not intended to limit the disclosed aspects and features of the invention to the specified embodiments or to usage only with the illustrated medical line. Those of skill in the art will recognize that the disclosed aspects and features of the invention are not limited to any particular embodiment of a securement device, and securement devices which include one or more of the inventive aspects and features herein described can be designed for use with a variety of medical articles.

Figure 1:
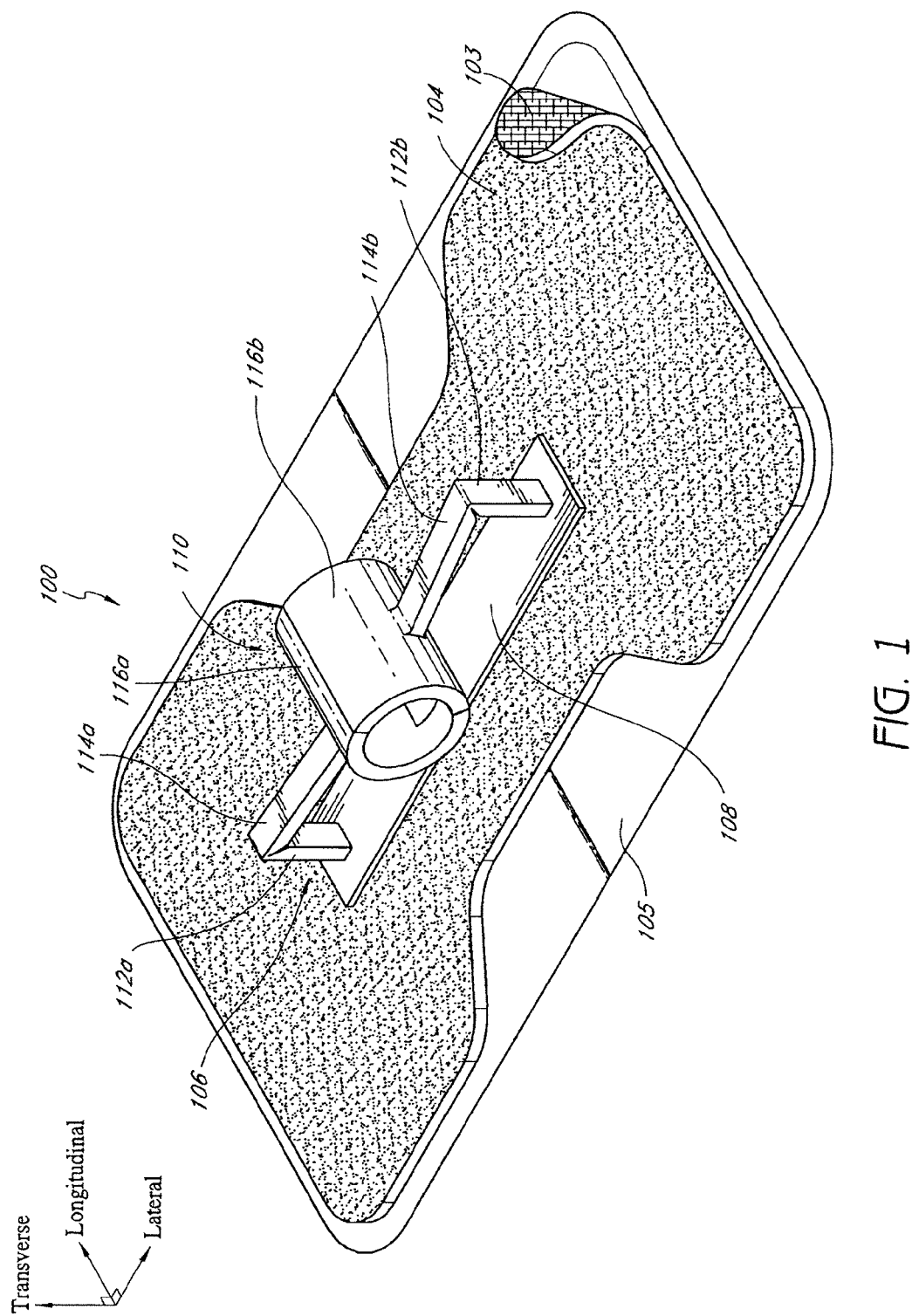
FIG. 1 is a perspective view of a securement device configured in accordance with a preferred embodiment of the present invention.

To assist in the description of the components of the securement system, the following coordinate terms are used (see FIG. 1). A "longitudinal axis" is generally parallel to a portion of the medical line or other medical article retained by the securement device, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or of the medical article, and therefore is substantially synonymous with the term "longitudinal" as used herein. Also, the terms "proximal" and "distal", which are used to describe the present securement device, are used consistently with the description of the exemplary applications (i.e., the illustrative example of the use application). Thus, proximal and distal are used in reference to the center of the patient's body. The terms "upper," "lower," "top," "bottom," "underside," "upperside" and the like, which also are used to describe the present securement device, are used in reference to the illustrated orientation of the embodiment. Brief introductions to some of the features, which are common to the described embodiments of the securement devices, are now described.

The preferred embodiments of the present invention advantageously provide a securement device for securing a medical article to a patient. The medical article preferably has an elongated body. The securement device includes a retainer which is movable between an open position, in which the retainer can receive the medical article, and a closed position, in which the retainer limits or arrests movement of the medical article in at least one direction, i.e., longitudinal, lateral, and transverse directions. In each of the embodiments described below, the retainer employs a toggle clamp mechanism to aid in closing of the retainer and securement of the medical article. The retainer moves from the open position to the closed position when the medical article is placed in the retainer and gentle force is applied.

FIG. 1 illustrates a medical line securement device 100 configured according to an embodiment and shown in closed position. The device 100 generally includes an anchor pad 104 and a retainer 106. The anchor pad 104 may comprise one or more types of adhesive 103 on all or a portion of its bottom surface. The anchor pad 104 may also be provided with a removable liner 105, comprising a polyester film or other suitable material, which is configured to protect the adhesive 103 prior to application of the anchor pad 104 to a patient's skin. The anchor pad 104 may comprise a flexible material configured to conform to the contours of the patient's body at the attachment surface. The anchor pad 104 may have any shape or configuration consistent with its intended use, including but not limited to the illustrated configuration.

The retainer 106 has a base 108 disposed on the anchor pad 104 and a clamp structure 110 disposed on the base 108. The base 108 can be attached to the anchor pad using adhesive or any other suitable means. The base 108 is configured to provide support and rigidity to the clamp structure 110, and can comprise any suitable material, such as, for example, a semi-rigid or rigid plastic. The base 108 extends between two spaced-apart supports 112(a), 112(b) which extend generally in a transverse direction from the base 108. The base 108 can be a thin, flat, and rigid member extending along the anchor pad 104 between the supports 112(a), 112(b). In certain embodiments, the base can extend laterally and/or longitudinally beyond the proximal ends of the supports 112(a), 112(b). In some embodiments, the base 108 can be curved somewhat in a transverse direction to conform to the contours of a patient's body. Reinforcements can be provided between the supports and the base and configured to resist or limit bending of the supports in the lateral and/or longitudinal directions.

As shown in the figure, the supports 112(a), 112(b) extend generally perpendicularly from the base 108. Alternatively, the supports 112(a), 112(b) can be angled laterally outward (away from each other) or inward (toward each other), preferably within the same plane, in the open position. The supports 112(a), 112(b) can have any configuration suitable for their intended use. For example, the supports 112(a), 112(b) can comprise posts or walls having any suitable cross sectional shape, such as a rectangular or circular shape. The supports 112(a), 112(b) can also have a constant or variable cross section. For example, the supports 112(a), 112(b) can have a wider cross section closer to the base, and a narrower cross section near their distal ends. The supports 112(a), 112(b) can be integrally formed with the base, or can be formed separately and attached to the base using adhesive or other suitable means. The supports 112(a), 112(b) can be configured with sufficient rigidity to resist bending in the longitudinal and transverse directions, while allowing some elastic deformation to occur in the lateral direction when a given amount of force is applied. Alternatively, the supports 112(a), 112(b) can be substantially rigid in all three directions. The supports 112(a), 112(b) can be fixed with respect to the base. Alternatively, the supports 112(a), 112(b) can be configured to be movable with respect to the base, such that their distal ends can move between first and second lateral positions.

Each of the supports 112(a), 112(b) is coupled at its distal end to a lever arm 114(a), 114(b). The lever arms 114(a), 114(b) extend laterally toward each other from the distal ends of the supports 112(a), 112(b). Each of the lever arms 114(a), 114(b) includes a channel portion 116(a), 116(b) at their distal ends. The channel portions 116(a), 116(b) face toward each other and, in the closed position, cooperate to secure a medical line in position.

Figure 2:
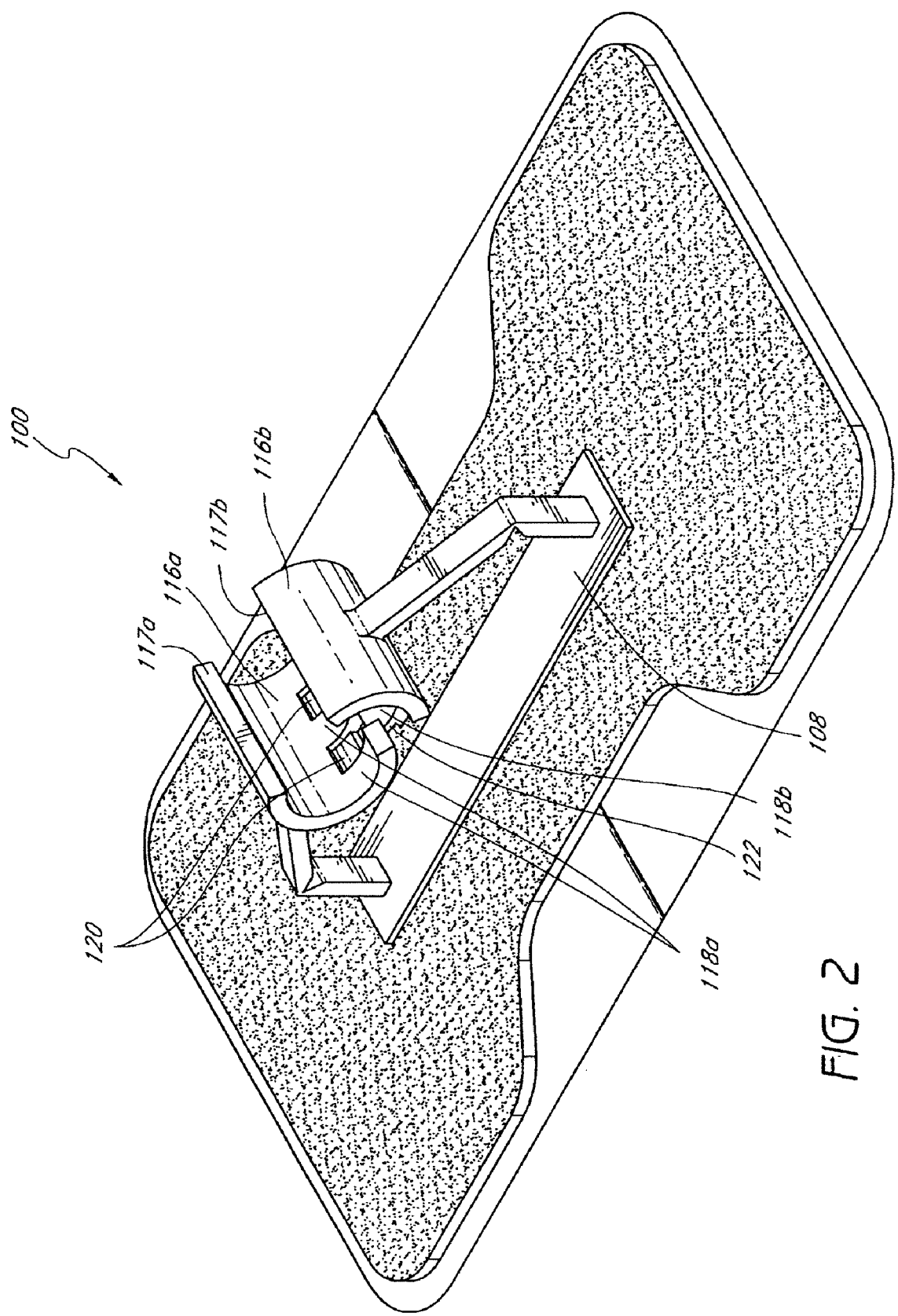
FIG. 2 is a perspective view of the securement device of FIG. 1 shown in an open position, with lever arms extending upwardly from side supports.

As can be seen in FIG. 2, the channel portions 116(a), 116(b) have upper edges 117(a), 117(b) which, in the open position, are spaced apart by an amount sufficient to allow placement of the medical line between the channel portions 116(a), 116(b). The medical line may be lowered between the upper edges 117(a), 117(b) or inserted between the channel portions 116(a), 116(b) along the longitudinal axis.

As also shown in FIG. 2, the left channel portion 116(a) includes teeth 118(a) which are spaced apart to receive corresponding teeth 118(b) of the right channel portion 116(b). Such a configuration allows the channel portions 116(a), 116(b) to move relative to one another in a transverse direction, without substantial interference, from the open position toward a closed position. The teeth 118(a), 118(b) assist in the alignment of the channel portions 116(a), 116(b) as the lever arms 114(a), 114(b) are moved toward the clamped position. The left channel portion 116(a) also includes one or more lands 120 disposed between the teeth 118(a). The teeth 118(b) of the right channel portion 116(b) include laps 122 which correspond to the shape of the lands 120. As the channel portions 116(a), 116(b) are moved toward the closed position (see FIGS. 5-7), the lands 120 are placed in abutting relationship with the laps 122 in the teeth 118(b) of the right channel portion 116(b). Although the illustrated embodiment includes lands only in the left channel portion 116(a) and corresponding laps only in the right channel portion 116(b), alternative embodiments can include corresponding lands and laps on one or both channel portions.

Figure 3:
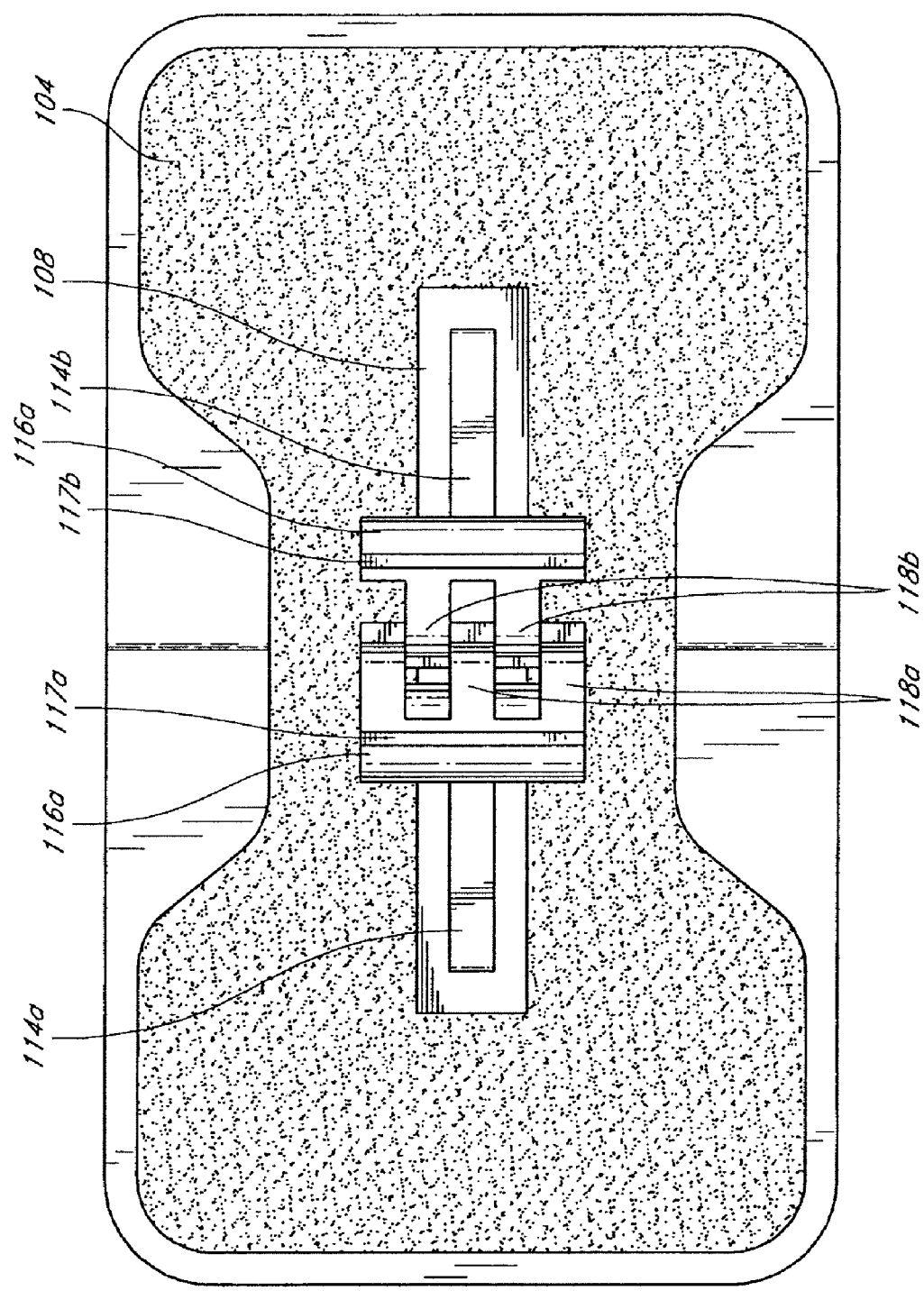
FIG. 3 is a top plan view of the securement device of FIG. 1 in an open position.
Figure 4:
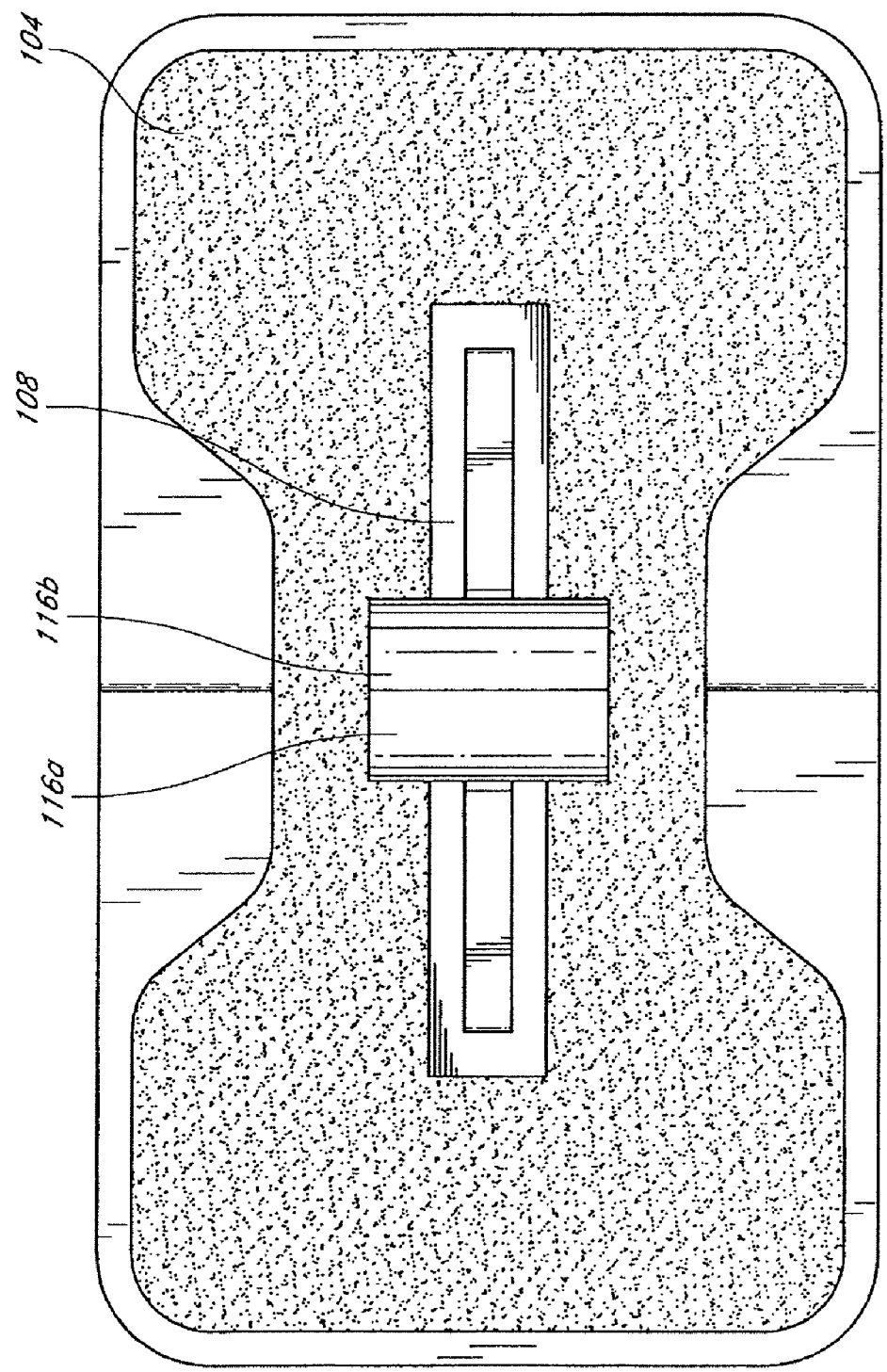
FIG. 4 is a top plan view of the securement device of FIG. 1 in a closed position.

FIGS. 3 and 4 show top plan views of the device 100 in open (FIG. 3) and clamped (FIG. 4) positions. The channel portions 116(a), 116(b) extend in a longitudinal direction beyond the straight portions of the lever arms 114(a), 114(b). In the open position, the upper edges 117(a), 117(b) of the channel portions 116(a), 116(b) are spaced apart to allow placement of the medical line therebetween, while the teeth 118(a), 118(b) intersect to form a receiving area for the medical line. In the closed position, the channel portions can extend entirely around the medical line. In alternative embodiments, however, the channel portions can extend only partially around the medical line in the closed position. For example, the channel portions can extend between 180 and 360 degrees about the medical line.

With reference now to FIG. 5, the lever arms 114(a), 114(b) are configured to pivot about pivot points 124(a), 124(b). The lever arms 114(a), 114(b) can be independently movable, or their movement may be coupled, for example by interengaging structure in the channel portions of each lever arm 114(a), 114(b). The lever arms 114(a), 114(b) can be integrally formed with the supports and configured to pivot about the distal ends of the supports, or the lever arms 114(a), 114(b) can be formed separately and pivotably coupled to the supports in any suitable fashion. The lever arms 114(a), 114(b) can be configured with sufficient thickness and rigidity to resist bending along the straight portions of the arms in the longitudinal, lateral, and transverse directions as the arms move from an open position through a horizontal position and into a clamped position.

The supports 112(a), 112(b) are notched at their distal ends to facilitate movement of the lever arms 114(a), 114(b) between an open and a closed position, while at the same time providing a stop to limit motion of the lever arms 114(a), 114(b) past the closed position. The pivot points 124(a), 124(b) are disposed in line with one another, equidistant from the base 108, providing the outer pivot points for the clamp structure 110.

In the open position, as shown in FIG. 5, the pivot points 124(a), 124(b) are spaced apart from each other by a distance B, and are spaced apart from the base 108 by a distance C. The lever arms 114(a), 114(b) extend laterally and upwardly from the supports 112(a), 112(b), toward each other and away from the base 108. The upper edges 117(a), 117(b) of the channel portions 116(a), 116(b) are spaced apart to allow for placement of the medical line between the channel portions 116(a), 116(b), while the teeth 118(a), 118(b) in the lower parts of the channel portions 116(a), 116(b) cooperate to receive the medical line and prevent it from passing all the way through the channel portions 116(a), 116(b). As the medical line is received between the channel portions 116(a), 116(b) and gentle downward force is applied, the clamp structure 110 begins to move downward and close about the medical line.

FIG. 6 illustrates the clamp structure 110 in an intermediate and horizontal position. The lever arms 114(a), 114(b) and channel portions 116(a), 116(b) are configured such that the maximum interference between the channel portions 116(a), 116(b) occurs in this position. In the illustrated embodiment, such interference occurs as a result of the abutting relationship between the lands 120 and laps 122 in the channel portions 116(a), 116(b). The lever arms 114(a), 114(b) and channel portions 116(a), 116(b) are dimensioned such that, when they are moved to the intermediate horizontal position, they have a combined length B' which is greater than the spacing B of the pivot points 124(a), 124(b) in the open position. As a result, in the intermediate position, the supports 112(a), 112(b) may elastically deform somewhat in an outward direction.

FIG. 7 illustrates the clamp structure 110 in a clamped (over-center) position in which the channel portions 116(a), 116(b) are configured to at least partially surround the medical line so as to limit movement of the line in the transverse and lateral directions. In this position, the clamp structure 110 is also configured to limit longitudinal movement of the line by squeezing the medical line. A friction enhancing material may be applied to the surface of the channel portions 116(a), 116(b) to inhibit movement of the medical line in the longitudinal direction. For example, the channel portions can include adhesive. Additionally or alternatively, the channel portions can be provided with one or more protrusions configured to grip the line with the device is in the closed position.

To release the clamp structure 110 from the clamped position, a sufficient force is applied generally in the transverse direction to move the lever arms 114(a), 114(b) through the intermediate (center) position (see FIG. 6). In the clamped position, the lever arms 114(a), 114(b) can be angled downward, toward the base 108, and the channel portions 116(a), 116(b) cooperate to define a center pivot point 126. The center pivot point 126 is spaced apart from the base 108 by a distance C' which is shorter than the distance C (that is, the center pivot point is spaced closer to the base 108 than are the outer pivot points 124(a), 124(b)). Any deformation that may have occurred in the supports 112(a), 112(b) in the intermediate position is relaxed, and the pivot points 124(a), 124(b) are returned to their original positions. The lever arms move in both lateral and transverse directions to capture the medical article between the channel portions as the lever arms move from the open position, through the intermediate position, and into the closed position.

Figure 8B:
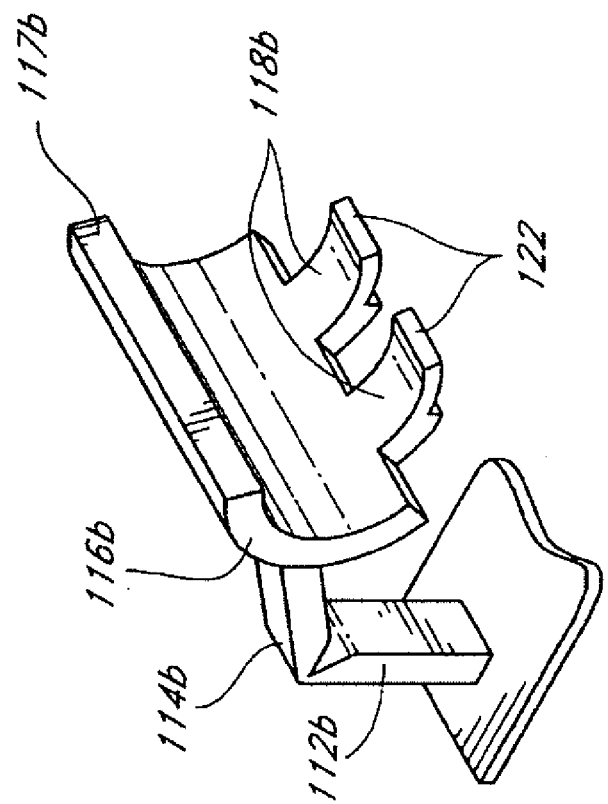
FIG. 8B is a partially cut away perspective view of the rightmost portion of the clamp structure shown in FIG. 2.
Figure 8A:
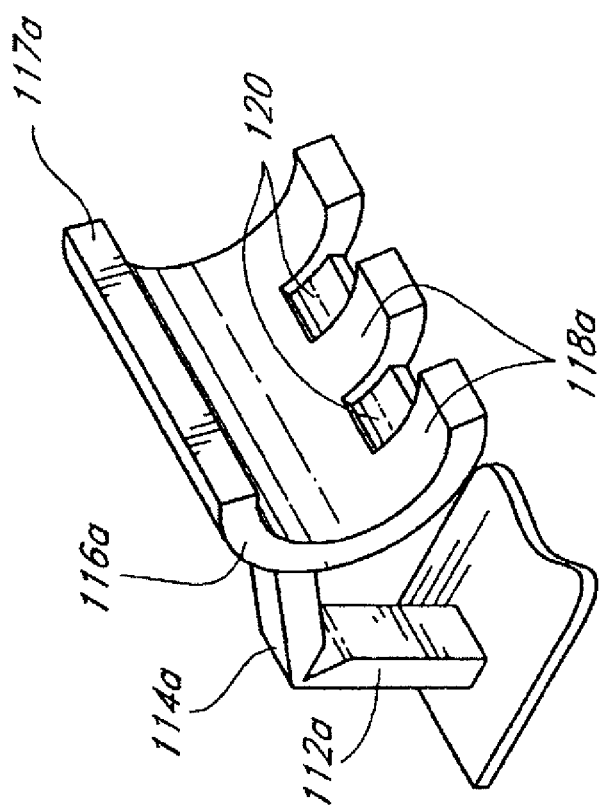
FIG. 8A is partially cut away perspective view of the leftmost portion of the clamp structure shown in FIG. 2.

FIGS. 8A and 8B illustrate the configuration of the left channel portion 116(a) (FIG. 8A) and the right channel portion 116(b) (FIG. 8B). Although illustrated with two separate channel portions connected to the lever arms, embodiments can include a single channel section connected to both lever arms between the supports. The left and right channel portions can have corresponding slots and teeth, as shown in the illustrated embodiment, which are configured to facilitate independent movement of the channel portions. Additionally or alternatively, the channel portions can be connected or attached at a hinge point so that their movement is coupled. The channel portion or portions can also be provided with one or more additional features to limit at least longitudinal movement of the line. For example, the channel portions can include adhesive. Additionally or alternatively, the channel portions can be provided with one or more protrusions or indentations configured to grip the line with the device is in the closed position. The channel portion or portions can also have one or more slots configured to receive corresponding structure in a fitting on a medical line so as to limit longitudinal movement of the line once it is placed in the channel.

To use the device 100 in a medical application, a medical practitioner may first establish the appropriate position of an indwelling medical line relative to a patient, according to known procedures. The practitioner may then remove the liner 105 from the anchor pad 104 and place the pad 104 on the patient's skin at an appropriate position, for example near the insertion site. The pad 104 may be positioned so that the channel portions 116(a), 116(b) extend toward the insertion site.

Next, the practitioner places the medical line between the channel portions 116(a), 116(b) so that it contacts the teeth 118(a), 118(b) in the lower parts of the channel portions 116(a), 116(b). The practitioner may then press down on the medical line, causing the lever arms 114(a), 114(b) to move downward, and causing the channel portions 116(a), 116(b) to close around the medical line. The practitioner may apply enough pressure to move the clamp structure 110 through the horizontal position, in which the combined length of the lever arms 114(a), 114(b) and the channel portions 116(a), 116(b) is greater than the original spacing of the pivot points 124(a), 124(b), to the over-center and clamped position described above in connection with FIG. 7. As the clamp structure 110 moves through the horizontal position and the outward forces on the supports 112(a), 112(b) are relaxed, the clamp structure 110 may "pop" or "snap" into the clamped position, indicating to the practitioner to the device has been properly closed around the medical line. Alternatively, the practitioner may secure the retainer 106 to the medical line prior to placing the anchor pad 104 on the patient.

Figure 9:
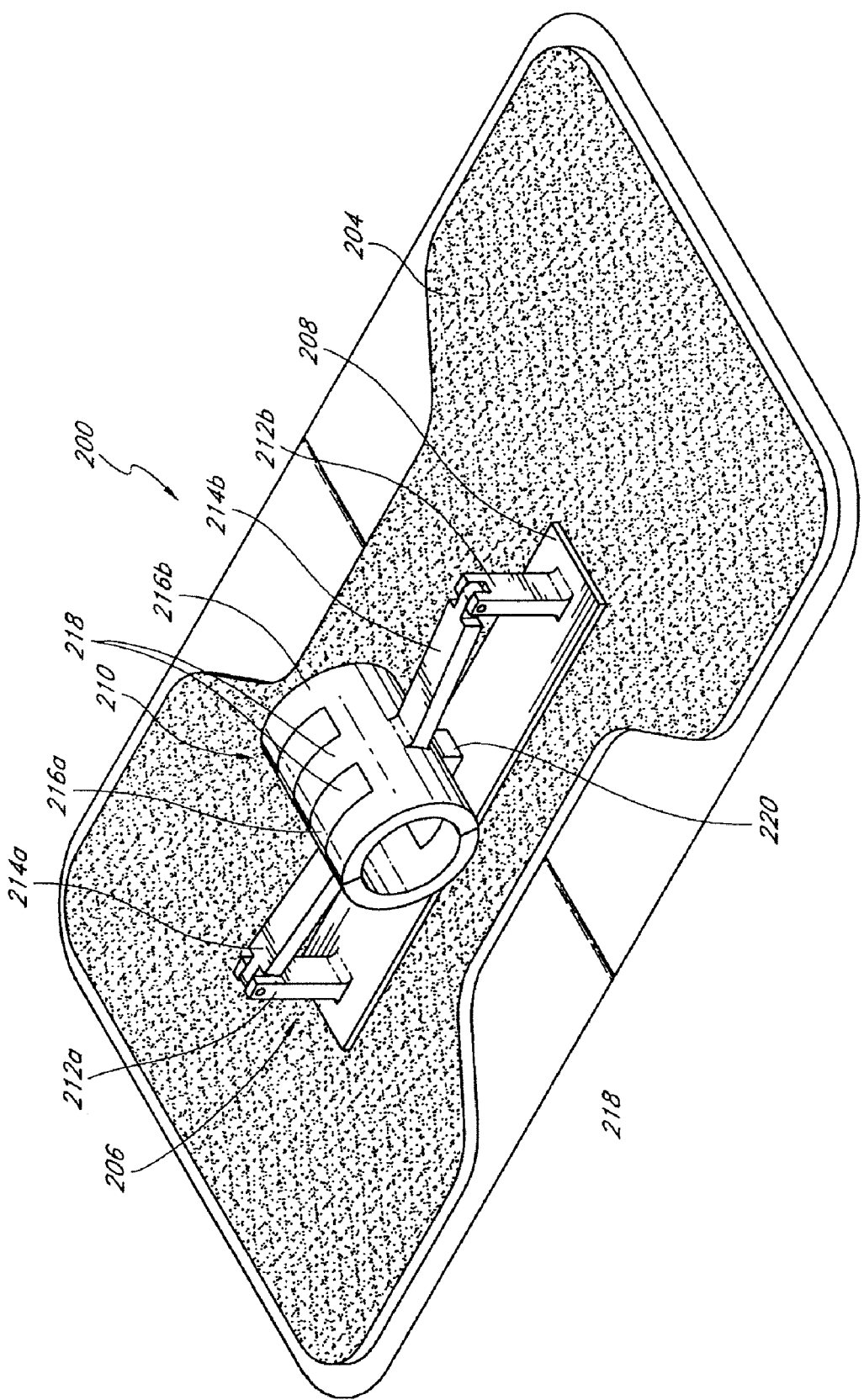
FIG. 9 is a perspective view of a securement device configured in accordance with another preferred embodiment of the present invention.

With reference now to FIG. 9, a securement device 200 according to another embodiment is described. The device 200 generally includes an anchor pad 204 and a retainer 206. The retainer 206 includes a base 208 disposed on the anchor pad 206 and a clamp structure 210 disposed on the base 208. The clamp structure 210 includes two spaced-apart supports 212(a), 212(b) extending generally upwardly from the base 208. Each of the supports 212(a), 212(b) is coupled at its distal end to a lever arm 214(a), 214(b) via a hinge mechanism. The lever arms 214(a), 214(b) extend laterally toward one other from the distal ends of the supports 212(a), 212(b). Each of the lever arms 214(a), 214(b) includes a channel portion 216(a), 216(b). The channel portions 216(a), 216(b) face generally toward each other and, in the closed position, cooperate to secure a medical line in position. The channel portions 216(a), 216(b) can include interengaging teeth 218 extending both above and below the lever arms 214(a), 214(b). The channel portions 216(a), 216(b) can be provided with lands and laps, as described above in connection with FIGS. 1-8, or other features configured to abut one another when the lever arms 214(a), 214(b) are moved to a horizontal position. The base 208 also includes a stop member 220 which is configured to limit motion of the channel portions 216(a), 216(b) past the closed position (see FIG. 11).

FIG. 10 shows the device 200 in an open position, in which the upper edges of the channel portions 216(a), 216(b) are spaced apart by an amount sufficient to allow placement of a medical line therebetween. The supports 212(a), 212(b) include pivot points 222(a), 222(b) at their distal ends. The channel portions 216(a), 216(b) move with the lever arms

214(*a*), 214(*b*) as the lever arms pivot about points 222(*a*), 222(*b*). Although not shown, the channel portions 216(*a*), 216(*b*) can include interengaging structure configured to couple the transverse motion of the left and right lever arms 214(*a*), 214(*b*). As the device 200 moves from the open position to the closed position (see FIG. 11), the clamp structure 210 passes through a horizontal position in which the lever arms 214(*a*), 214(*b*) have a combined length which is greater than the lateral spacing of the pivot points 222(*a*), 222(*b*) in the open position. The lever arms 214(*a*), 214(*b*) thus apply an outwardly-directed force to the supports 212(*a*), 212(*b*) in the horizontal position. This force is relaxed somewhat as the device 200 is moved to the closed position illustrated in FIG. 11.

In the embodiments described above, the outer pivot points of the clamping structures are essentially fixed, and move laterally only slightly as the clamping structure moves through an intermediate and horizontal position. As shown in FIGS. 12-14, however, embodiments of the invention also include clamping structures in which the outer pivot points are movable in a lateral direction. With reference now to FIG. 12, a device 300 is illustrated in an open position. The device 300 includes an anchor pad 304, a base 308 disposed on the anchor pad 304, and a clamp structure 310 disposed on the base 308. The clamp structure 310 includes two spaced-apart supports 312(*a*), 312(*b*) which extend upwardly from the base 308. In the open position, the supports 312(*a*), 312(*b*) are angled somewhat toward each other.

Each of the supports 312(*a*), 312(*b*) is coupled at its distal end to a lever arm 314(*a*), 314(*b*). The lever arms 314(*a*), 314(*b*) are pivotable about outer pivot points 324(*a*), 324(*b*) at the distal ends of the supports 312(*a*), 312(*b*). The pivot points 324(*a*), 324(*b*) are spaced apart from the base 308 by a distance D. The supports 312(*a*), 312(*b*) are notched at their distal ends to facilitate movement of the lever arms 314(*a*), 314(*b*) between an open and a closed position, while at the same time providing a stop to limit motion of the lever arms 314(*a*), 314(*b*) past the closed position (see FIG. 14). The lever arms 314(*a*), 314(*b*) extend laterally toward each other from the distal ends of the supports 312(*a*), 312(*b*), and are connected to each other between the supports 312(*a*), 312(*b*) at a center pivot point 326. Each of the lever arms 314(*a*), 314(*b*) includes a straight portion 315(*a*), 315(*b*) and a channel portion 316(*a*), 316(*b*). In the open position, the upper edges of the channel portions 316(*a*), 316(*b*) are spaced apart by an amount sufficient to allow placement of a medical line therebetween. The channel portions 316(*a*), 316(*b*) face toward each other and move with the lever arms 314(*a*), 314(*b*) as they pivot about the outer pivot points 324(*a*), 324(*b*).

When the device 300 is in the open position, the pivot points 324(*a*), 324(*b*) are spaced apart by a distance E. The straight portions 315(*a*), 315(*b*) of the lever arms 314(*a*), 314(*b*) each have a length F. The distance E between the pivot points 324(*a*), 324(*b*) is smaller than the combined length 2F of the straight portions 315(*a*), 315(*b*) of the lever arms 314(*a*), 314(*b*), so that when the clamp structure 310 is moved to a horizontal position, the pivot points 324(*a*), 324(*b*) are moved laterally outward. FIG. 13 illustrates the clamp structure 310 in the intermediate and horizontal position. As shown in the figure, the supports 312(*a*), 312(*b*) are elastically deformed in a laterally outward direction.

FIG. 14 illustrates the clamp structure 310 in a clamped (over-center) position in which the channel portions 316(*a*), 316(*b*) are configured to at least partially surround a medical line so as to limit movement of the line in the longitudinal and lateral directions. In this position, the clamp structure is also configured to limit transverse movement of the line. To release the clamp structure 310 from the clamped position, a sufficient force must be applied in the transverse direction to move the lever arms 314(*a*), 314(*b*) through the intermediate (center) position (see FIG. 13). In the clamped position, the lever arms 314(*a*), 314(*b*) are angled slightly toward the base 308, and the center pivot point 326 is spaced apart from the base 108 by a distance D' which is shorter than the distance D (that is, the center pivot point is spaced closer to the base 308 than are the outer pivot points 324(*a*), 324(*b*)). As shown in the figure, the elastic deformation of the supports 312(*a*), 312(*b*) is also relaxed somewhat when the device 300 is in the clamped position.

FIGS. 15 and 16 illustrate a securement device 400 according to a further embodiment. The device 400 includes an anchor pad 404, a base 408 disposed on the anchor pad 404, and a clamp structure 410 disposed on the base 408. The clamp structure 410 includes two spaced-apart supports 412(*a*), 412(*b*) which extend upwardly from the base 408. Lever arms 414(*a*), 414(*b*) are coupled to the distal ends of the supports 412(*a*), 412(*b*). The lever arms 414(*a*), 414(*b*) are pivotable about pivot points 424(*a*), 424(*b*) in the supports 412(*a*), 412(*b*). The supports 412(*a*), 412(*b*) are provided near their distal ends with stops 413, which are configured to limit movement of the lever arms 414(*a*), 414(*b*) past the closed position. The lever arms 414(*a*), 414(*b*) are connected at their distal ends to channel portions 416(*a*), 416(*b*). As shown in the figure, the distal end of the left channel portion 416(*a*) is connected to the proximal end of the right channel portion 416(*b*) at a pivot point 426. In the open position, the distal end of the right channel portion 416(*b*) and the proximal end of the left channel portion 416(*a*) are spaced apart by an amount sufficient to allow placement of a medical line in between the channel portions 416(*a*), 416(*b*). The distal end of the left lever arm 414(*a*) and the distal end of the right channel portion 416(*b*) include cooperating features 417(*a*), 417(*b*) configured to latch together when the device 400 is in the closed position. FIG. 16 illustrates the securement device 400 in the closed (clamped) position.

Figure 17:
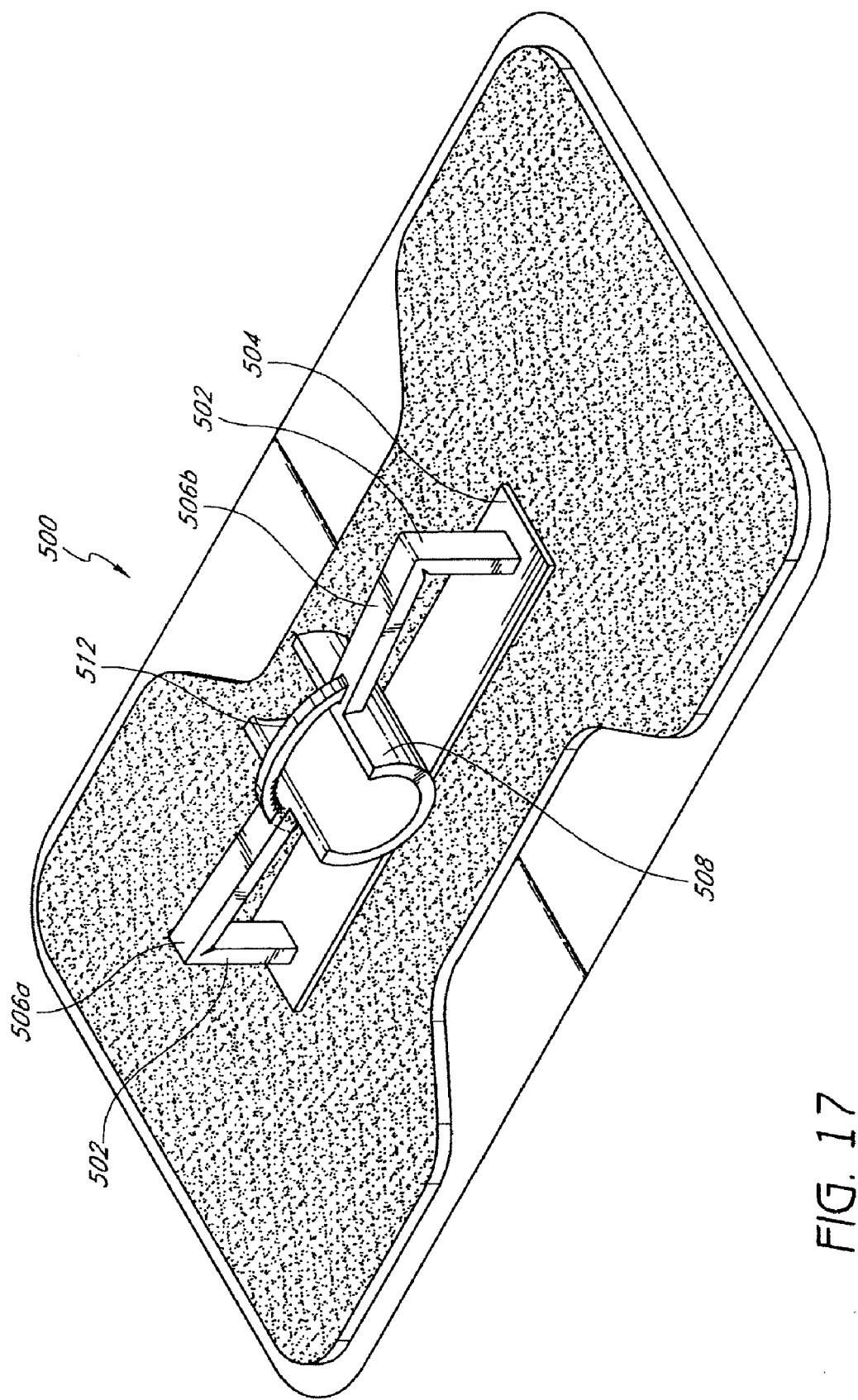
FIG. 17 is a perspective view of a securement device configured in accordance with another preferred embodiment of the present invention.

FIGS. 17-19 illustrate a securement device 500 according to an alternative embodiment. The device 500 includes two spaced-apart supports 502 extending from a base 504. A lever arm 506(*a*), 506(*b*) extends laterally from the distal end of each support 502. The lever arms 506(*a*), 506(*b*) are connected, between the supports 502, by a channel portion 508 which in the closed position shown in FIG. 17 is configured to at least partially surround and secure a medical line.

As shown in FIG. 18, in the open position, the supports 502 can be angled laterally inward as they extend from the base 504. The supports 502 are rigid and are configured to be movable with respect to the base 504, within a limited range of motion. The lever arms 506(*a*), 506(*b*) are pivotable about the distal ends 507 of the supports 502, also within a limited range of motion, between an open and closed position. In the open position, the distal ends 507 of the supports 502 are spaced apart by a distance G. The channel portion 508 is flexible to allow the lever arms 506(*a*), 506(*b*) to move between the open and closed positions, and has a shallower curvature in the open position than it does in the closed position (see FIG. 19). In the open position, the upper ends of the channel portion 508 are spaced apart by a distance greater than a diameter of the medical line, so as to receive the medical line within the channel portion 508.

The lever arms 506(*a*), 506(*b*) are rigid and substantially inflexible so as to resist bending in the longitudinal and transverse directions. The lever arms 506(*a*), 506(*b*) and the channel portion 508 are configured such that, when the lever arms 506(a), 506(b) are moved downward from an open position into horizontal alignment, the arms 506(a), 506(b) exert an outward force on the distal ends 507 of the supports 502. In the closed position, as illustrated in FIG. 19, the lever arms 506(a), 506(b) are angled slightly downward, and the supports 502 are moved outwardly, so that the distal ends 507 of the supports 502 are spaced apart by a distance F' which is greater than the spacing G of the ends 507 in the open position. In the closed position, the channel portion 508 has a tighter curvature than in the open position, and is configured to extend for at least 180° about the medical line.

The device 500 can include a latch or other mechanism which extends over the medical line and provides additional securement when the device 500 is in the closed position. The latch may be a ratcheting latch, such as the ratcheting latch 512 shown in FIG. 19. The ratcheting latch 512 extends from the right lever arm 506(b) and is movable with respect to the lever arm 506(b). The left lever arm 506(a) is provided with an opening 514 configured to receive the distal end of the ratcheting latch 512. The distal end of the latch 512 is provided with teeth 516 that cooperate with features in the opening 514 to tighten the latch 512 over the medical line. The latch 512 is configured to maintain the relative positions of the lever arms 506(a), 506(b) and hold the device 500 in a closed position. Although not illustrated, the portion of the latch 512 located over the channel portion 508 can also be provided with one or more protrusions or other features configured to resist movement of the medical line in a longitudinal direction.

Figure 20:
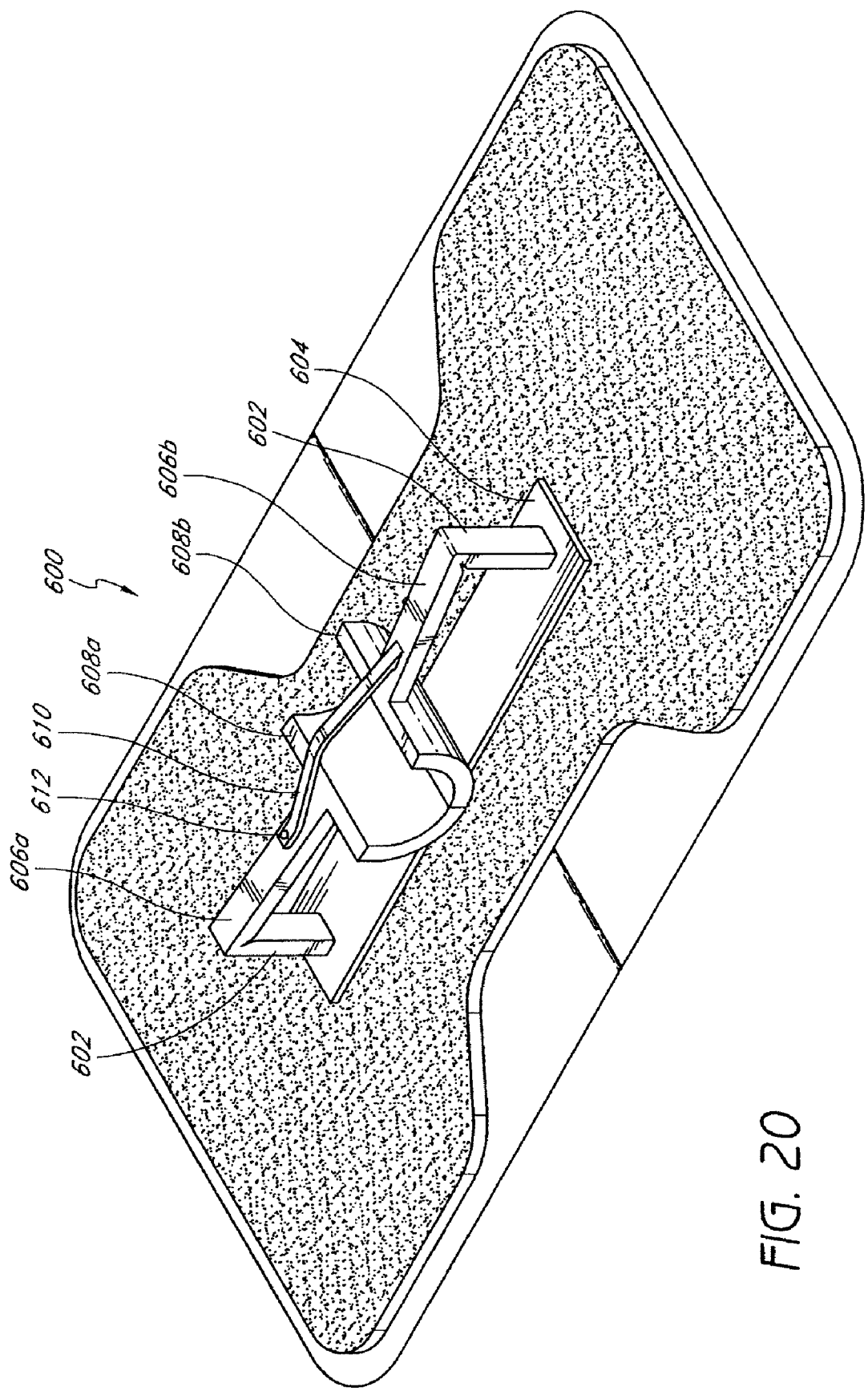
FIG. 20 is a perspective view of a securement device configured in accordance with another preferred embodiment of the present invention.
Figure 21:
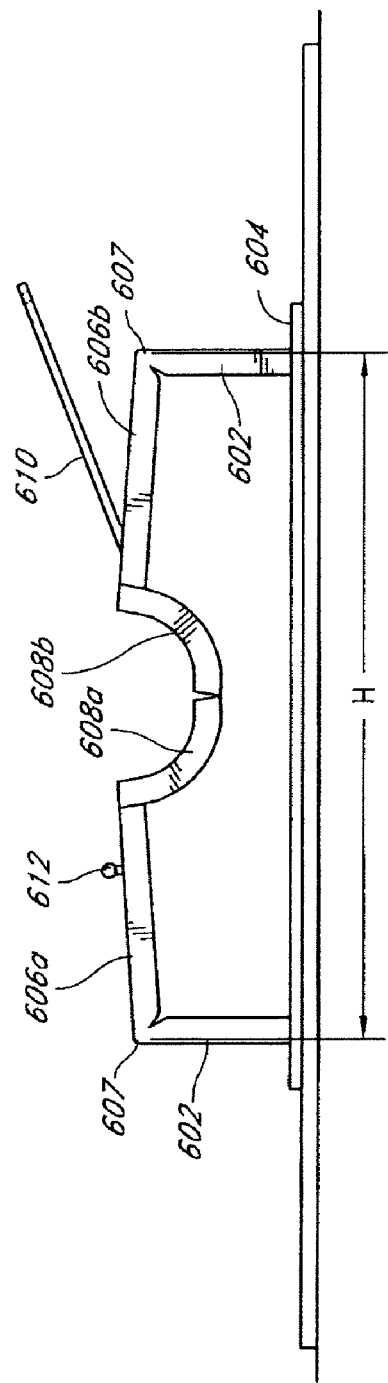
FIG. 21 is a front view of the device of FIG. 20 shown in an open position.
Figure 22:
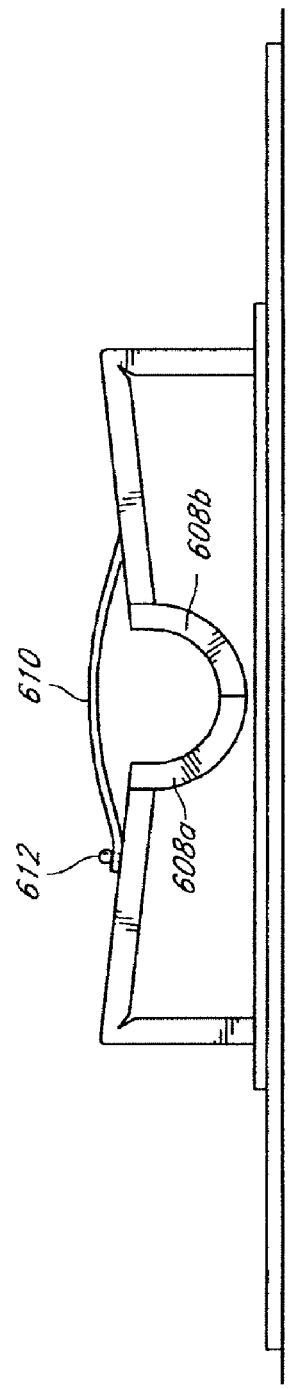
FIG. 22 is a front view of the device of FIG. 20 shown in a locked or clamped position.

FIGS. 20-22 illustrate a securement device 600 according to another embodiment of the present invention. The device 600 includes two spaced-apart supports 602 extending upwardly from a base 604. A lever arm 606(a), 606(b) extends laterally from the distal end of each support 602. The lever arms 606(a), 606(b) each include a channel portion 608(a), 608(b). The channel portions 608(a), 608(b) are hinged together or otherwise movably coupled between the supports 602.

The lever arms 606(a), 606(b) are pivotable about the distal ends 607 of the supports 602 between an open and closed position. In the open position, as illustrated in FIG. 21, the distal ends 607 of the supports 602 are spaced apart from each other by a distance H, and the lever arms 606(a), 606(b) extend laterally and upwardly from the distal ends 607. As the device 600 is moved from the open position to the closed position illustrated in FIG. 22, the lever arms 606(a), 606(b) pass through an intermediate position in which the straight portions of the lever arms 606(a), 606(b) are horizontally aligned and in which the channel portions 608(a), 608(b) are disposed in abutting relationship. In the intermediate position, the lever arms 606(a), 606(b) have a combined length (measured laterally) which is at least slightly greater than the spacing H of the distal ends of the supports 602 in the open position. Thus, as the lever arms 606(a), 606(b) pass through the intermediate position, they exert an outwardly directed force on the distal ends 607 of the supports 602, causing the distal ends 607 of the supports 602 to elastically deform in a laterally outward direction. Both the lever arms 606(a), 606(b) and the channel portions 608(a), 608(b) have a substantially rigid configuration so as to transmit these outward forces to the supports 602.

In the closed position, the lever arms 606(a), 606(b) extend downward from the distal ends 607 of the supports 602, and the outward forces on the ends 607 are at least partially relaxed. Thus, in the closed position, the distal ends 607 of the supports 602 may return to (or move closer to) their original positions. The undersides of the channel portions 608(a), 608(b) may approach or touch the base 604 in the closed position.

The device 600 can include a latch 610 configured to hold the device 600 in the closed position. The latch 610 extends from the right lever arm 606(b) and is pivotable or otherwise movable in a lateral direction between an unlatched position and a latched position in which the latch extends laterally over the channel portions 608(a), 608(b). The latch is configured to engage with a cooperating protrusion 612 on the left lever arm 606(a) to maintain the device 600 in a clamped or closed position.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present anchor has been described in the context of particularly preferred embodiments, the skilled artisan will appreciate, in view of the present disclosure, that certain advantages, features and aspects of the anchor may be realized in a variety of other applications, many of which have been noted above. For example, while particularly useful for small-scale applications, such as the illustrated medical application, the skilled artisan can readily adopt the principles and advantages described herein to a variety of other applications, including larger scale devices.

Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A securement device for securing a medical article, the device comprising:
   a base;
   first and second supports extending away from the base, each of the first and second supports having a distal end which is spaced apart from the base;
   a first lever arm pivotable about the distal end of the first support, the first lever arm comprising a first channel portion;
   a second lever arm pivotable about the distal end of the second support, the second lever arm comprising a second channel portion;
   the first and second lever arms being movable between an open position, in which the first and second lever arms extend above a line defined by the distal ends of the supports, and a closed position, in which the first and second lever arms extend below the line, the first and second channel portions cooperating to define a receiving area for the medical article when in the open position and cooperating to at least partially surround the medical article when in the closed position, the distal ends of the supports being spaced laterally from the first and second channel portions when the first and second lever arms are in both the open and closed positions.

2. The securement device of claim 1, wherein the supports in the open position extend normal to the base.

3. The securement device of claim 2, wherein the supports in the closed position are angled laterally outward.

4. The securement device of claim 1, wherein the supports in the open position are angled laterally inward.

5. The securement device of claim 1, wherein the distal ends of the first and second supports are spaced apart laterally by a first distance in the open position, the supports passing through an intermediate position as they move towards the closed position, the supports being spaced apart by a second distance in the intermediate position, the second distance being greater than the first distance.

6. The securement device of claim 1, wherein the first and second lever arms are independently movable.

7. The securement device of claim 1, wherein the first and second lever arms are pivotably coupled.

8. The securement device of claim 7, wherein a distal end of the first channel portion is pivotably coupled to a distal end of the second channel portion.

9. The securement device of claim 7, wherein a distal end of the first channel portion is pivotably coupled to a proximal end of the second channel portion.

10. The securement device of claim 7, wherein a distal end of a straight portion of the first lever arm is pivotably coupled to a distal end of a channel portion of the second lever arm.

11. The securement device of claim 7, wherein a distal end of a straight portion of the first lever arm is pivotably coupled to a distal end of a straight portion of the second lever arm.

12. The securement device of claim 1, wherein each of the first and second lever arms comprises a substantially straight portion.

13. The securement device of claim 12, wherein the first and second lever arms pass through an intermediate position as they move from the open position to the closed position, the straight portions of the first and second lever arms being aligned with one another and exerting a lateral force on the distal ends of the first and second supports in the intermediate position.

14. The securement device of claim 13, wherein the distal ends of the first and second supports are elastically deformed in a lateral direction in at least the intermediate position.

15. The securement device of claim 14, wherein the distal ends of the first and second supports are elastically deformed in a lateral direction in the closed position.

16. The securement device of claim 1, wherein the first and second lever arms define a center pivot point in at least the closed position, the center pivot point being lower than the line defined by the distal ends of the first and second supports when the device is in the closed position.

17. The securement device of claim 1, wherein at least one of the first and second channel portions includes an adhesive.

18. The securement device of claim 1, wherein the first and second channel portions are continuous with one another.

19. The securement device of claim 1, further comprising a latch configured to secure the device in the closed position.

20. The securement device of claim 19, wherein the latch is a ratcheting latch.

21. The securement device of claim 19, wherein the latch includes one or more protrusions configured to grip the medical article when the device is in the closed position.

22. A retainer for securing a medical article, the retainer comprising:
a base;
a first support extending from the base;
a second support extending from the base;
a first lever arm coupled to the first support at a first point;
a second lever arm coupled to the second support at a second point; and
at least one channel portion coupled to at least one of the first and second lever arms, at least a portion of the retainer being movable between a first position, in which the first and second lever arms extend generally upward of the first and second points, and a second position, in which the first and second lever arms extend generally downward of the first and second points, the first and second points moving away and then towards each other in a lateral direction when the retainer moves from the first position to the second position, the at least one channel portion being configured to at least partially surround the medical article when the retainer is in the second position.

23. The retainer of claim 22, wherein the at least one channel portion is coupled to both the first and second lever arms.

24. The retainer of claim 22, wherein the at least one channel portion is flexible.

25. The retainer of claim 22, wherein the device comprises two channel portions, each channel portion being coupled to one of the first and second lever arms.

26. The retainer of claim 25, wherein the two channel portions are pivotably connected.

27. A securement device for securing a medical article, the device comprising:
a retainer having a first portion and a second portion disposed above a base, the first and second portions being movable in at least a transverse direction with respect to first and second points to define an open position and a closed position, the first and second points being spaced apart from the base, the first and second portions extending generally away from the first and second points when in the open position, the first and second portions extending generally downwardly from the first and second points when in the closed position, the first and second portions causing the first and second points to move laterally outward as the first and second portions move from the open position to the closed position, the first and second portions defining a channel having a central axis in the closed position, the channel being configured to at least partially surround the medical article in the closed position, the central axis being closer to the base than the first and second points at least when the retainer is in the closed position.

28. A method of securing a medical article to a patient, the method comprising:
providing a retainer comprising a base, first and second supports extending upwardly from the base, a first lever arm pivotable about a distal region of the first support, a second lever arm pivotable about a distal region of the second support, a first channel portion movable with the first lever arm, a second channel portion movable with the second lever arm, the first and second lever arms being movable between an open position, in which the first and second lever arms extend above a line defined by the distal ends of the supports, and a closed position, in which the first and second lever arms extend below the line, the first and second channel portions configured to allow placement of the medical article therebetween in the open position, the first and second channel portions cooperating to at least partially surround the medical article in the closed position;

placing the medical article between at least portions of the first and second channel portions when in an open position; and applying downward force on at least one of the medical article and the retainer so as to move the lever arms past an intermediate position in which the lever arms are horizontally aligned and into the closed position, the lever arms exerting a laterally outward force on the distal regions of the first and second supports at least when the lever arms are horizontally aligned.

29. A securement device for securing a medical article, the device comprising:
a base;
a first support member extending from the base and having a distal end;
a second support member extending from the base and having a distal end, the second support member being spaced apart from the first support member;
a first arm member being pivotable about the first support member;
a second arm member being pivotable about the second support member;
at least a portion of each of the first and second arm members cooperating to define a channel, the channel being spaced from the distal ends of the first and second support members,
at least a portion of the device being movable between a first position in which the channel is configured to allow ingress of at least a portion of the medical article therein and in which a lower portion of the channel is disposed above the distal ends of the first and second support members, and a second position in which the channel is configured to at least partially surround the portion of the medical article and in which the lower portion of the channel is disposed below the distal ends of the first and second support members.

30. The securement device of claim 29, wherein the first arm member is connected to the second arm member.

31. The securement device of claim 30, wherein the first arm member and the second arm member are hingedly connected.

32. The securement device of claim 30, wherein the first arm member and the second arm member are connected along a longitudinal axis.

33. The securement device of claim 32, wherein the longitudinal axis is movable in at least a transverse direction between the first and second positions.

34. The securement device of claim 29, wherein each of the first support member and the second support member comprises a post.

35. The securement device of claim 29, wherein each of the first support member and the second support member comprises a wall.

36. The securement device of claim 29, wherein the first support member and the second support member each have a longitudinal length less than a longitudinal length of the portion of each of the first and second arm members which defines the channel.

37. The securement device of claim 29, wherein at least a portion of each of the first and second support members has a circular cross-sectional shape.

38. The securement device of claim 29, wherein the first and second support members are fixed with respect to the base.

39. The securement device of claim 29, wherein the base is contoured.

40. The securement device of claim 29, wherein the base extends in a lateral direction beyond the proximal ends of the first and second support members.

41. The securement device of claim 29, wherein the channel has a smaller cross-sectional area in the second position than in the first position.

42. The securement device of claim 29, further comprising a friction enhancing material disposed on a surface of the channel.

43. The securement device of claim 42, wherein the friction enhancing material is disposed so as to contact at least a portion of the medical article at least when the device is in the second position.

* * * * *